United States Patent
Kristensen et al.

(10) Patent No.: US 12,127,734 B2
(45) Date of Patent: Oct. 29, 2024

(54) APPARATUS AND METHOD FOR 3D SURGICAL IMAGING

(71) Applicant: Cilag GmbH International, Zug (CH)

(72) Inventors: Marco D. F. Kristensen, San Francisco, CA (US); Kevin A. Kauffman, Cincinnati, OH (US); Jeffrey S. Swayze, West Chester, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/733,343

(22) Filed: Apr. 29, 2022

(65) Prior Publication Data

US 2023/0346211 A1 Nov. 2, 2023

(51) Int. Cl.
| | |
|---|---|
| *A61B 1/00* | (2006.01) |
| *A61B 1/05* | (2006.01) |
| *A61B 1/313* | (2006.01) |
| *A61B 1/32* | (2006.01) |
| *A61B 17/34* | (2006.01) |

(52) U.S. Cl.
CPC ........ *A61B 1/3132* (2013.01); *A61B 1/00193* (2013.01); *A61B 1/05* (2013.01); *A61B 1/32* (2013.01); *A61B 17/34* (2013.01)

(58) Field of Classification Search
CPC ............ A61B 1/3132; A61B 17/00234; A61B 17/0485; A61B 17/0218; A61B 1/32; A61B 1/00087; A61B 1/053; A61B 17/3421; A61B 1/00154; A61B 2034/302; A61B 17/3478; A61B 2017/3405; A61B 17/3439; A61B 90/361; A61B 2017/00867; A61B 2017/06104; A61B 2017/2212; A61B 2017/22035; A61B 2017/00473; A61B 2017/3443; A61B 17/22031; A61B 2090/034; A61B 1/0005; A61B 1/00009; A61B 1/044; A61B 1/018; A61B 1/00045; A61B 1/00194; A61B 1/0605; A61B 1/00193; A61B 1/313; G06T 15/20; G06T 2210/41; H04N 13/282

See application file for complete search history.

(56) References Cited

U.S. PATENT DOCUMENTS

| | | | | |
|---|---|---|---|---|
| 5,209,735 A | * | 5/1993 | Lazarus | A61B 17/3421 604/170.01 |
| 5,320,611 A | * | 6/1994 | Bonutti | A61M 25/06 604/530 |

(Continued)

FOREIGN PATENT DOCUMENTS

WO WO-2012028840 A1 * 3/2012 ......... A61B 10/0048

*Primary Examiner* — Timothy J Neal
(74) *Attorney, Agent, or Firm* — Frost Brown Todd LLP

(57) ABSTRACT

A surgical imaging device includes a rigid body. The rigid body includes an elongate member extending longitudinally along a central axis to a sharp distal tip. The sharp distal tip is configured to pierce through tissue to access an interior of a cavity of a patient. The rigid body also includes a bore extending longitudinally through at least a portion of the elongate member. The surgical imaging device further includes a camera secured to the elongate member of the rigid body within the bore of the rigid body. The camera is adapted to capture images of the interior of the cavity of the patient when the sharp distal tip has pierced through the tissue to access the interior of the cavity of the patient.

20 Claims, 9 Drawing Sheets

(56) References Cited

U.S. PATENT DOCUMENTS

| | | | |
|---|---|---|---|
| 6,527,704 B1* | 3/2003 | Chang | A61B 17/3421 600/138 |
| 8,504,136 B1* | 8/2013 | Sun | A61B 5/1076 600/407 |
| 9,274,046 B2 | 3/2016 | Stewart et al. | |
| 10,792,069 B2 | 10/2020 | Hall et al. | |
| 10,820,924 B2 | 11/2020 | Hall et al. | |
| 11,000,270 B2 | 5/2021 | Scheib et al. | |
| 11,033,182 B2 | 6/2021 | Hansen et al. | |
| 11,039,734 B2 | 6/2021 | Hansen et al. | |
| 11,571,205 B2 | 2/2023 | Scheib et al. | |
| 11,754,712 B2 | 9/2023 | Scheib | |
| 2005/0107743 A1* | 5/2005 | Fangrow, Jr. | A61M 5/158 604/164.01 |
| 2005/0288622 A1* | 12/2005 | Albrecht | A61M 13/003 604/23 |
| 2006/0015068 A1* | 1/2006 | Amisar | A61M 25/0637 604/164.01 |
| 2010/0081875 A1* | 4/2010 | Fowler | A61B 1/041 600/114 |
| 2010/0292724 A1* | 11/2010 | Ravikumar | A61B 17/29 606/205 |
| 2012/0078236 A1* | 3/2012 | Schoepp | A61B 90/50 606/1 |
| 2013/0079597 A1* | 3/2013 | Auerbach | A61B 17/3474 600/204 |
| 2016/0278694 A1* | 9/2016 | Aharoni | A61B 5/6848 |
| 2017/0238962 A1* | 8/2017 | Hansen | A61B 1/05 |
| 2018/0103979 A1* | 4/2018 | Arimitsu | A61B 10/0233 |
| 2018/0189966 A1* | 7/2018 | Kamen | A61B 5/0084 |
| 2020/0015899 A1 | 1/2020 | Scheib et al. | |
| 2020/0015900 A1 | 1/2020 | Scheib et al. | |
| 2020/0015924 A1 | 1/2020 | Scheib et al. | |
| 2023/0156174 A1 | 5/2023 | Kristensen et al. | |

* cited by examiner

APPARATUS AND METHOD FOR 3D SURGICAL IMAGING

BACKGROUND

Surgical systems may incorporate an imaging system, which may allow the clinician(s) to view the surgical site and/or one or more portions thereof on one or more displays such as a monitor. The display(s) may be local and/or remote to a surgical theater. An imaging system may include a scope with a camera that views the surgical site and transmits the view to a display that is viewable by the clinician. Scopes include, but are not limited to, laparoscopes, robotic laparoscopes, arthroscopes, angioscopes, bronchoscopes, choledochoscopes, colonoscopes, cytoscopes, duodenoscopes, enteroscopes, esophagogastro-duodenoscopes (gastroscopes), endoscopes, laryngoscopes, nasopharyngo-neproscopes, sigmoidoscopes, thoracoscopes, ureteroscopes, and exoscopes. Imaging systems may be limited by the information that they are able to recognize and/or convey to the clinician(s). For example, limitations of cameras used in capturing images may result in reduced image quality.

Examples of surgical imaging systems are disclosed in U.S. Pat. Pub. No. 2020/0015925, entitled "Combination Emitter and Camera Assembly," published Jan. 16, 2020, issued as U.S. Pat. No. 11,754,712 on Sep. 12, 2023; U.S. Pat. Pub. No. 2020/0015923, entitled "Surgical Visualization Platform," published Jan. 16, 2020, issued as U.S. Pat. No. 11,000,270 on May 11, 2021; U.S. Pat. Pub. No. 2020/0015900, entitled "Controlling an Emitter Assembly Pulse Sequence," published Jan. 16, 2020; U.S. Pat. Pub. No. 2020/0015899, entitled "Surgical Visualization with Proximity Tracking Features," published Jan. 16, 2020, now abandoned; U.S. Pat. Pub. No. 2020/0015924, entitled "Robotic Light Projection Tools," published Jan. 16, 2020, now abandoned; and U.S. Pat. Pub. No. 2020/0015898, entitled "Surgical Visualization Feedback System," published Jan. 16, 2020, issued as U.S. Pat. No. 11,571,205 on Feb. 7, 2023. The disclosure of each of the above-cited U.S. patents and patent applications is incorporated by reference herein.

While various kinds of surgical instruments and systems have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
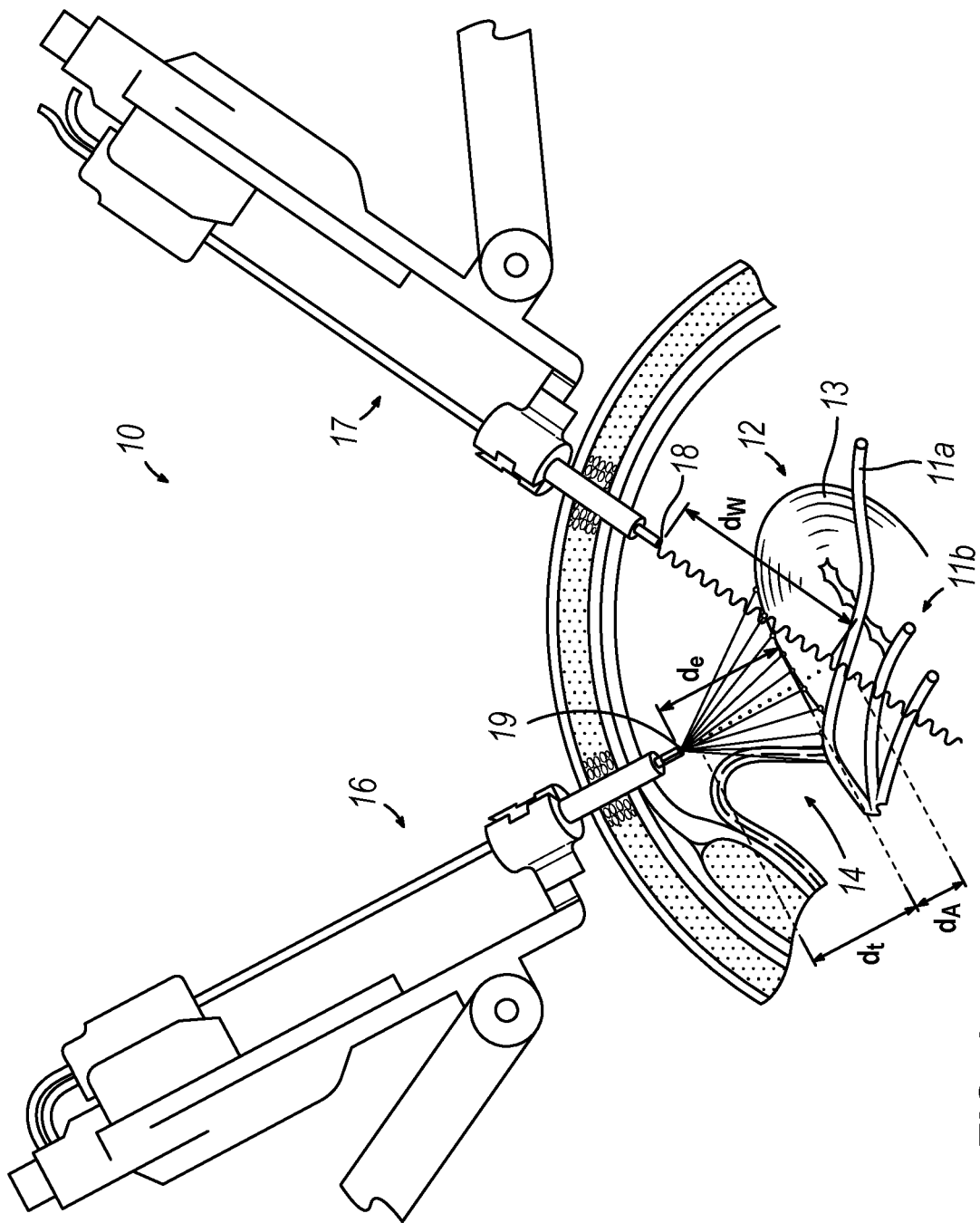
FIG. 1 depicts a schematic view of an exemplary surgical visualization system including an imaging device and a surgical device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical device. The term "proximal" refers to the position of an element arranged closer to the surgeon, and the term "distal" refers to the position of an element arranged further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose(s) described herein.

Similarly, the phrase "based on" should be understood as referring to a relationship in which one thing is determined at least in part by what it is specified as being "based on." This includes, but is not limited to, relationships where one thing is exclusively determined by another, which relationships may be referred to using the phrase "exclusively based on."

I. EXEMPLARY SURGICAL VISUALIZATION SYSTEM

FIG. 1 depicts a schematic view of a surgical visualization system (10) according to at least one aspect of the present disclosure. The surgical visualization system (10) may create a visual representation of a critical structure (11a, 11b) within an anatomical field. The surgical visualization system (10) may be used for clinical analysis and/or medical intervention, for example. In certain instances, the surgical visualization system (10) may be used intraoperatively to provide real-time, or near real-time, information to the clinician regarding proximity data, dimensions, and/or distances during a surgical procedure. The surgical visualization system (10) is configured for intraoperative identification of critical structure(s) and/or to facilitate the avoidance of critical structure(s) (11a, 11b) by a surgical device. For example, by identifying critical structures (11a, 11b), a clinician may avoid maneuvering a surgical device into a critical structure (11a, 11b) and/or a region in a predefined proximity of a critical structure (11a, 11b) during a surgical procedure. The clinician may avoid dissection of and/or near a vein, artery, nerve, and/or vessel, for example, identified as a critical structure (11a, 11b), for example. In various instances, critical structure(s) (11a, 11b) may be determined on a patient-by-patient and/or a procedure-by-procedure basis.

Critical structures (11a, 11b) may be any anatomical structures of interest. For example, a critical structure (11a, 11b) may be a ureter, an artery such as a superior mesenteric artery, a vein such as a portal vein, a nerve such as a phrenic nerve, and/or a sub-surface tumor or cyst, among other anatomical structures. In other instances, a critical structure (11a, 11b) may be any foreign structure in the anatomical field, such as a surgical device, surgical fastener, clip, tack, bougie, band, and/or plate, for example. In one aspect, a critical structure (11a, 11b) may be embedded in tissue. Stated differently, a critical structure (11a, 11b) may be positioned below a surface of the tissue. In such instances, the tissue conceals the critical structure (11a, 11b) from the clinician's view. A critical structure (11a, 11b) may also be obscured from the view of an imaging device by the tissue. The tissue may be fat, connective tissue, adhesions, and/or organs, for example. In other instances, a critical structure (11a, 11b) may be partially obscured from view. A surgical visualization system (10) is shown being utilized intraoperatively to identify and facilitate avoidance of certain critical structures, such as a ureter (11a) and vessels (11b) in an organ (12) (the uterus in this example), that are not visible on a surface (13) of the organ (12).

A. Overview of Exemplary Surgical Visualization System

With continuing reference to FIG. 1, the surgical visualization system (10) incorporates tissue identification and geometric surface mapping, potentially in combination with a distance sensor system (14). In combination, these features of the surgical visualization system (10) may determine a position of a critical structure (11a, 11b) within the anatomical field and/or the proximity of a surgical device (16) to the surface (13) of the visible tissue and/or to a critical structure (11a, 11b). The surgical device (16) may include an end effector having opposing jaws (not shown) and/or other structures extending from the distal end of the shaft of the surgical device (16). The surgical device (16) may be any suitable surgical device such as, for example, a dissector, a stapler, a grasper, a clip applier, a monopolar RF electrosurgical instrument, a bipolar RF electrosurgical instrument, and/or an ultrasonic instrument. As described herein, a surgical visualization system (10) may be configured to achieve identification of one or more critical structures (11a, 11b) and/or the proximity of a surgical device (16) to critical structure(s) (11a, 11b).

The depicted surgical visualization system (10) includes an imaging system that includes an imaging device (17), such as a camera or a scope, for example, that is configured to provide real-time views of the surgical site. In various instances, an imaging device (17) includes a spectral camera (e.g., a hyperspectral camera, multispectral camera, a fluorescence detecting camera, or selective spectral camera), which is configured to detect reflected or emitted spectral waveforms and generate a spectral cube of images based on the molecular response to the different wavelengths. Views from the imaging device (17) may be provided to a clinician; and, in various aspects of the present disclosure, may be augmented with additional information based on the tissue identification, landscape mapping, and input from a distance sensor system (14). In such instances, a surgical visualization system (10) includes a plurality of subsystems—an imaging subsystem, a surface mapping subsystem, a tissue identification subsystem, and/or a distance determining subsystem. These subsystems may cooperate to intraoperatively provide advanced data synthesis and integrated information to the clinician(s).

The imaging device (17) of the present example includes an emitter (18), which is configured to emit spectral light in a plurality of wavelengths to obtain a spectral image of hidden structures, for example. The imaging device (17) may also include a three-dimensional camera and associated electronic processing circuits in various instances. In one aspect, the emitter (18) is an optical waveform emitter that is configured to emit electromagnetic radiation (e.g., near-infrared radiation (NIR) photons) that may penetrate the surface (13) of a tissue (12) and reach critical structure(s) (11a, 11b). The imaging device (17) and optical waveform emitter (18) thereon may be positionable by a robotic arm or a surgeon manually operating the imaging device. A corresponding waveform sensor (e.g., an image sensor, spectrometer, or vibrational sensor, etc.) on the imaging device (17) may be configured to detect the effect of the electromagnetic radiation received by the waveform sensor.

The wavelengths of the electromagnetic radiation emitted by the optical waveform emitter (18) may be configured to enable the identification of the type of anatomical and/or physical structure, such as critical structure(s) (11a, 11b). The identification of critical structure(s) (11a, 11b) may be accomplished through spectral analysis, photo-acoustics, fluorescence detection, and/or ultrasound, for example. In one aspect, the wavelengths of the electromagnetic radiation may be variable. The waveform sensor and optical waveform emitter (18) may be inclusive of a multispectral imaging system and/or a selective spectral imaging system, for example. In other instances, the waveform sensor and optical waveform emitter (18) may be inclusive of a photoacoustic imaging system, for example. In other instances, an optical waveform emitter (18) may be positioned on a separate surgical device from the imaging device (17). By way of example only, the imaging device (17) may provide hyperspectral imaging in accordance with at least some of the teachings of U.S. Pat. No. 9,274,046, entitled "System and Method for Gross Anatomic Pathology Using Hyperspectral Imaging," issued Mar. 1, 2016, the disclosure of which is incorporated by reference herein in its entirety.

The depicted surgical visualization system (10) also includes an emitter (19), which is configured to emit a pattern of light, such as stripes, grid lines, and/or dots, to enable the determination of the topography or landscape of a surface (13). For example, projected light arrays may be used for three-dimensional scanning and registration on a surface (13). The projected light arrays may be emitted from an emitter (19) located on a surgical device (16) and/or an imaging device (17), for example. In one aspect, the projected light array is employed to determine the shape defined by the surface (13) of the tissue (12) and/or the motion of the surface (13) intraoperatively. An imaging device (17) is configured to detect the projected light arrays reflected from the surface (13) to determine the topography of the surface (13) and various distances with respect to the surface (13). By way of further example only, a visualization system (10) may utilize patterned light in accordance with at least some of the teachings of U.S. Pat. Pub. No. 2017/0055819, entitled "Set Comprising a Surgical Instrument," published Mar. 2, 2017, issued as U.S. Pat. No. 11,033,182 on Jun. 15, 2021, the disclosure of which is incorporated by reference herein in its entirety; and/or U.S. Pat. Pub. No. 2017/0251900, entitled "Real Time Correlated Depiction System fo a Surgical Tool," published Sep. 7, 2017, issued as U.S. Pat. No. 11,0394,734 on Jun. 22, 2021, the disclosure of which is incorporated by reference herein in its entirety.

The depicted surgical visualization system (10) also includes a distance sensor system (14) configured to determine one or more distances at the surgical site. In one aspect, the distance sensor system (14) may include a time-of-flight distance sensor system that includes an emitter, such as the structured light emitter (19); and a receiver (not shown), which may be positioned on the surgical device (16). In other instances, the time-of-flight emitter may be separate from the structured light emitter. In one general aspect, the emitter portion of the time-of-flight distance sensor system (14) may include a laser source and the receiver portion of the time-of-flight distance sensor system (14) may include a matching sensor. A time-of-flight distance sensor system (14) may detect the "time of flight," or how long the laser light emitted by the structured light emitter (19) has taken to bounce back to the sensor portion of the receiver. Use of a very narrow light source in a structured light emitter (19) may enable a distance sensor system (14) to determine the distance to the surface (13) of the tissue (12) directly in front of the distance sensor system (14).

Referring still to FIG. 1, a distance sensor system (14) may be employed to determine an emitter-to-tissue distance ($d_e$) from a structured light emitter (19) to the surface (13) of the tissue (12). A device-to-tissue distance ($d_t$) from the distal end of the surgical device (16) to the surface (13) of the tissue (12) may be obtainable from the known position of the emitter (19) on the shaft of the surgical device (16) relative to the distal end of the surgical device (16). In other words, when the distance between the emitter (19) and the distal end of the surgical device (16) is known, the device-to-tissue distance ($d_t$) may be determined from the emitter-to-tissue distance ($d_e$). In certain instances, the shaft of a surgical device (16) may include one or more articulation joints; and may be articulatable with respect to the emitter (19) and the jaws. The articulation configuration may include a multi-joint vertebrae-like structure, for example. In certain instances, a three-dimensional camera may be utilized to triangulate one or more distances to the surface (13).

As described above, a surgical visualization system (10) may be configured to determine the emitter-to-tissue distance ($d_e$) from an emitter (19) on a surgical device (16) to the surface (13) of a uterus (12) via structured light. The surgical visualization system (10) is configured to extrapolate a device-to-tissue distance ($d_t$) from the surgical device (16) to the surface (13) of the uterus (12) based on emitter-to-tissue distance ($d_e$). The surgical visualization system (10) is also configured to determine a tissue-to-ureter distance ($d_A$) from a ureter (11a) to the surface (13) and a camera-to-ureter distance ($d_w$), from the imaging device (17) to the ureter (11a). Surgical visualization system (10) may determine the camera-to-ureter distance ($d_w$), with spectral imaging and time-of-flight sensors, for example. In various instances, a surgical visualization system (10) may determine (e.g., triangulate) a tissue-to-ureter distance ($d_A$) (or depth) based on other distances and/or the surface mapping logic described herein.

B. Exemplary Control System

Figure 2:
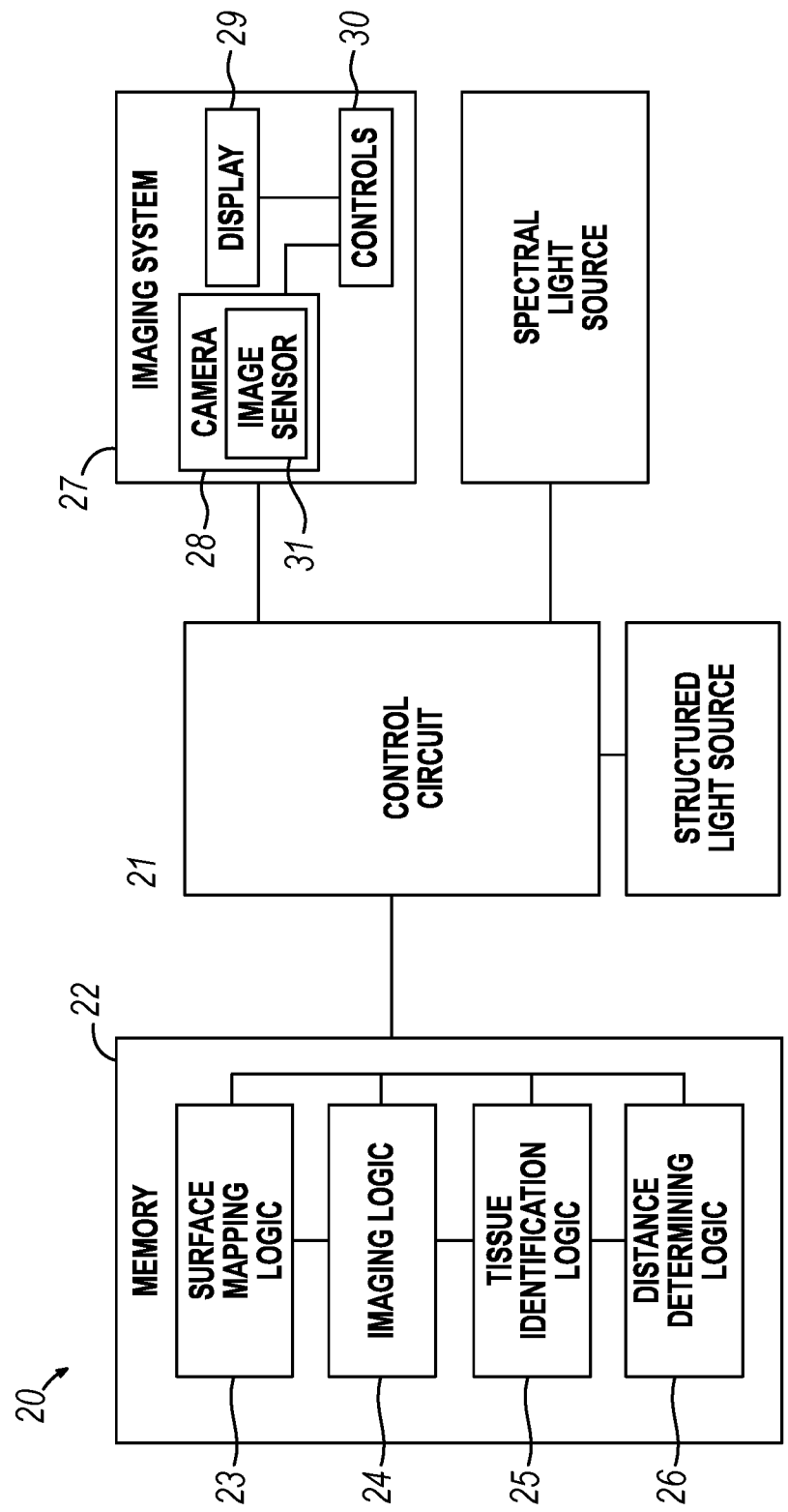
FIG. 2 depicts a schematic diagram of an exemplary control system that may be used with the surgical visualization system of FIG. 1.

FIG. 2 is a schematic diagram of a control system (20), which may be utilized with a surgical visualization system (10). The depicted control system (20) includes a control circuit (21) in signal communication with a memory (22). The memory (22) stores instructions executable by the control circuit (21) to determine and/or recognize critical structures (e.g., critical structures (11a, 11b) depicted in FIG. 1), determine and/or compute one or more distances and/or three-dimensional digital representations, and to communicate certain information to one or more clinicians. For example, a memory (22) stores surface mapping logic (23), imaging logic (24), tissue identification logic (25), or distance determining logic (26) or any combinations of logic (23, 24, 25, 26). The control system (20) also includes an imaging system (27) having one or more cameras (28) (like the imaging device (17) depicted in FIG. 1), one or more displays (29), one or more controls (30) or any combinations of these elements. The one or more cameras (28) may include one or more image sensors (31) to receive signals from various light sources emitting light at various visible and invisible spectra (e.g., visible light, spectral imagers, three-dimensional lens, among others). The display (29) may include one or more screens or monitors for depicting real, virtual, and/or virtually-augmented images and/or information to one or more clinicians.

In various aspects, a main component of a camera (28) includes an image sensor (31). An image sensor (31) may include a Charge-Coupled Device (CCD) sensor, a Complementary Metal Oxide Semiconductor (CMOS) sensor, a short-wave infrared (SWIR) sensor, a hybrid CCD/CMOS architecture (sCMOS) sensor, and/or any other suitable kind(s) of technology. An image sensor (31) may also include any suitable number of chips.

The depicted control system (20) also includes a spectral light source (32) and a structured light source (33). In certain instances, a single source may be pulsed to emit wavelengths of light in the spectral light source (32) range and wavelengths of light in the structured light source (33) range. Alternatively, a single light source may be pulsed to provide light in the invisible spectrum (e.g., infrared spectral light) and wavelengths of light on the visible spectrum. A spectral light source (32) may include a hyperspectral light source, a multispectral light source, a fluorescence excitation light source, and/or a selective spectral light source, for example. In various instances, tissue identification logic (25) may identify critical structure(s) via data from a spectral light source (32) received by the image sensor (31) portion of a camera (28). Surface mapping logic (23) may determine the surface contours of the visible tissue based on reflected structured light. With time-of-flight measurements, distance determining logic (26) may determine one or more distance(s) to the visible tissue and/or critical structure(s) (11a, 11b). One or more outputs from surface mapping logic (23), tissue identification logic (25), and distance determining logic (26), may be provided to imaging logic (24), and combined, blended, and/or overlaid to be conveyed to a clinician via the display (29) of the imaging system (27).

II. EXEMPLARY SURGICAL VISUALIZATION SYSTEM WITH MULTI-CAMERA IMAGE COMBINATION

Figure 3:
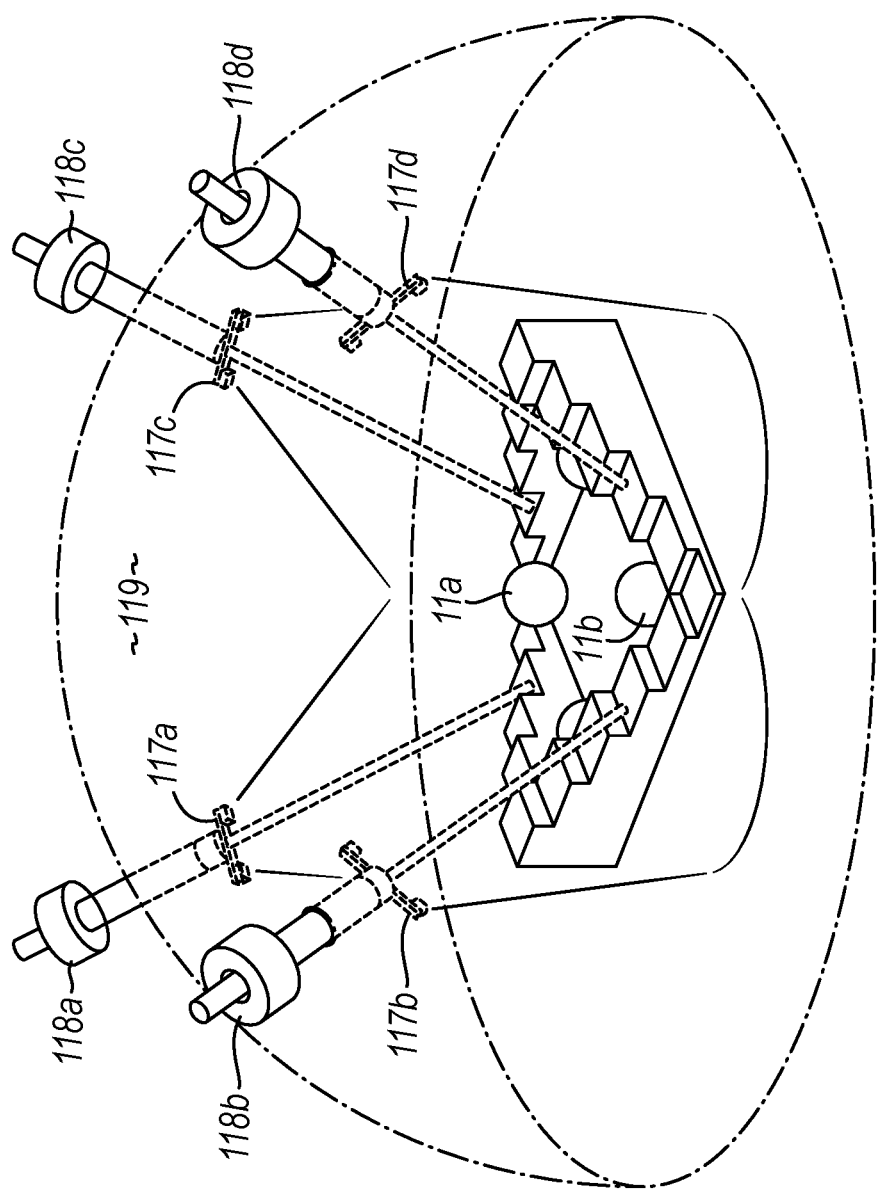
FIG. 3 depicts a scenario in which a plurality of imaging devices are used to gather data for an exemplary surgical visualization system.
Figure 4A:
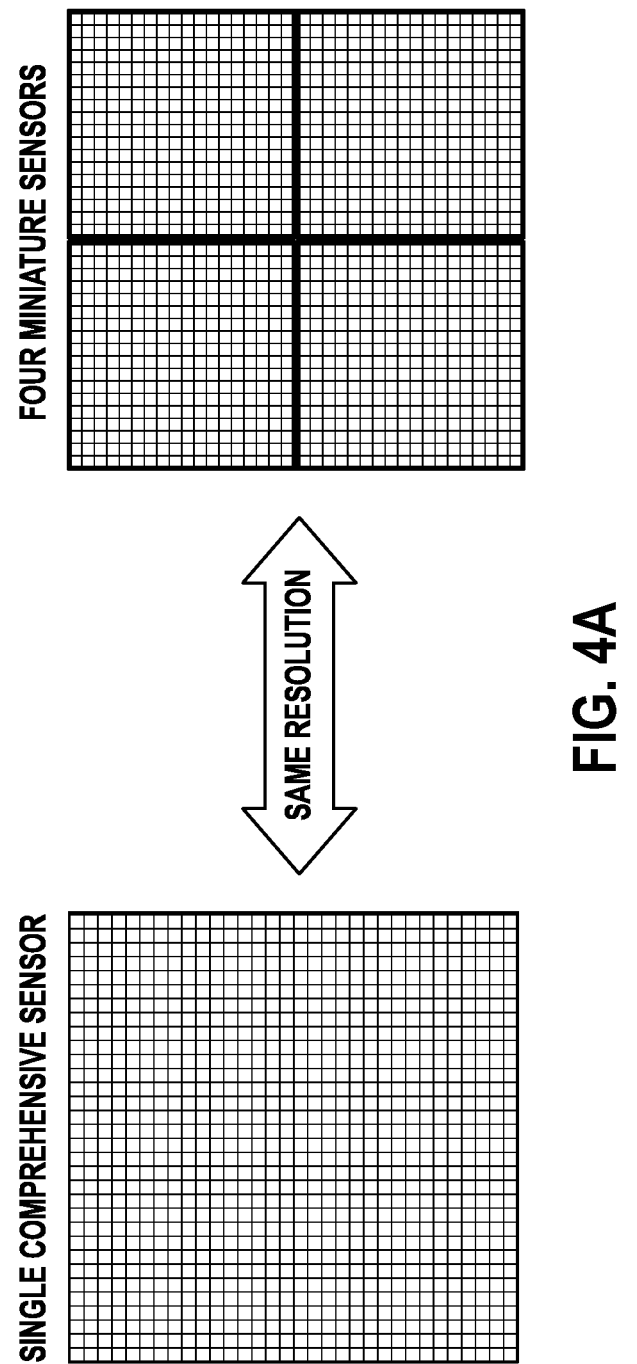
FIGS. 4A-4B depict relationships between images captured with a single imaging device and multiple imaging devices.
Figure 4B:
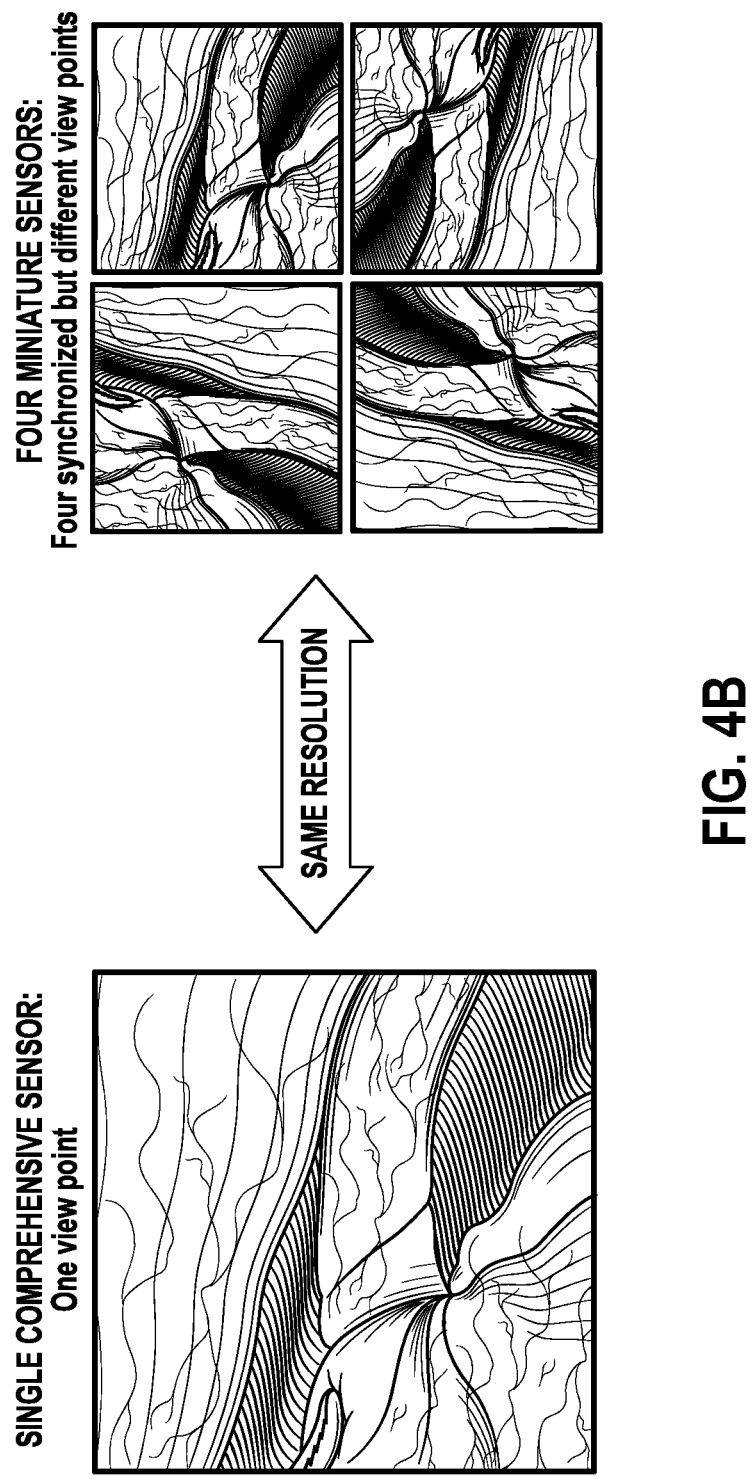
Figure 5:
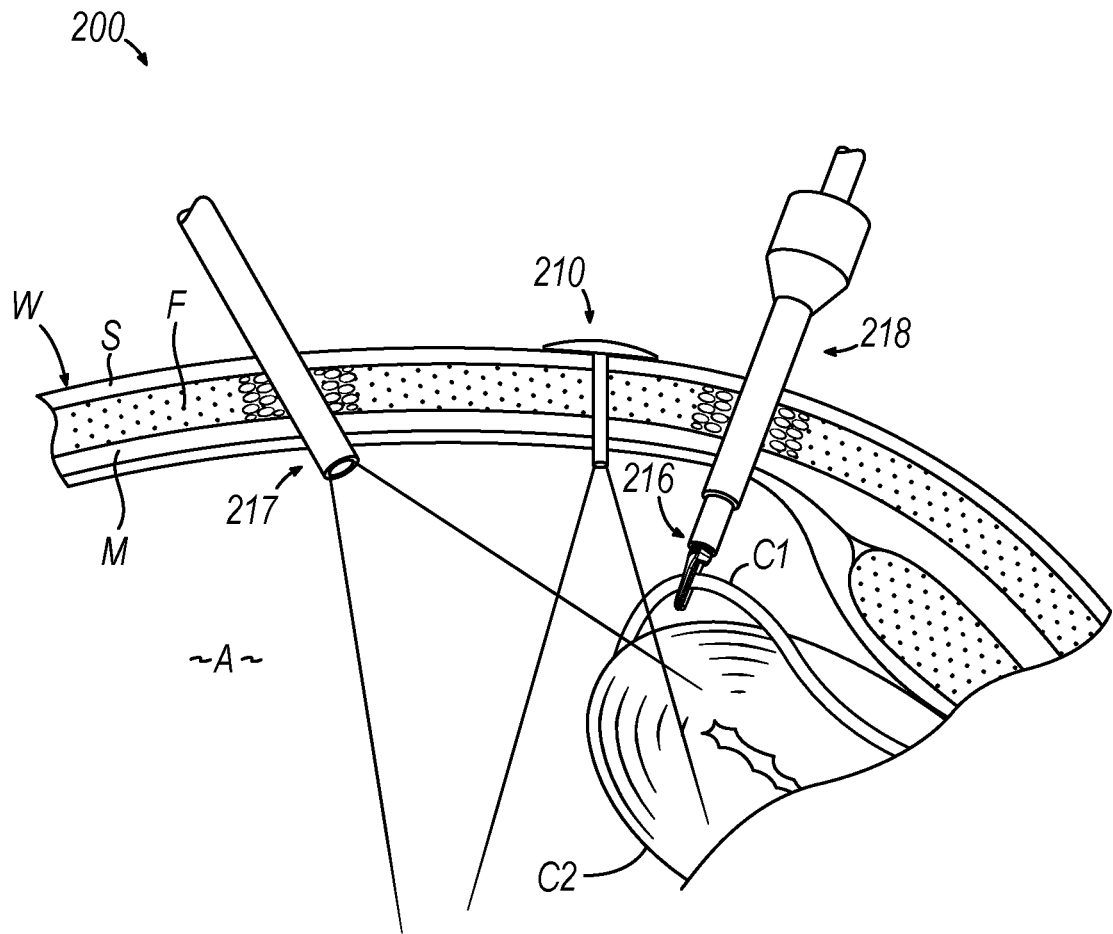
FIG. 5 depicts a schematic view of another exemplary surgical visualization system including a laparoscope and an imaging thumbtack.

In some cases, it may be desirable to combine data captured from multiple imaging devices to provide a more robust and versatile data set. To illustrate, consider a scenario such as shown in FIG. 3. FIG. 3 illustrates a scenario in which a plurality of imaging devices (117a, 117b, 117c, 117d) are at least partially inserted through corresponding trocars (118a, 118b, 118c, 118d) to capture images of an interior of a cavity of a patient (119). As shown in FIG. 3, each of the imaging devices (117a, 117b, 117c, 117d) has a corresponding field of view, and those fields of view overlap to provide a complete view of the portion of the interior of the cavity of the patient, including one or more critical structures (11a, 11b) (represented by spheres in FIG. 3). In such a case, image processing techniques such as bundle adjustment or other multi view geometry techniques may be used to combine the images captured by the various imaging devices (117a, 117b, 117c, 117d) to create a complete three-dimensional representation (e.g., a point cloud) of the relevant portion of the interior of the cavity of the patient (119). This, in turn, may allow for the imaging devices used in capturing the images to be smaller than would be the case if a single imaging device were relied on, as their combined viewpoints may allow for sufficient information to be captured despite the limitations of any individual device, as is shown in FIGS. 4A and 4B. This may allow, for example, imaging devices having a cross sectional area less than one square millimeter to be used. An example of such a device is the OV6948 offered by OmniVision Technologies, Inc., which measures 0.575 mm×0.575 mm, though the use of that particular imaging device is intended to be illustrative only, and should not be treated as implying limitations on the types of imaging devices which may be used in a scenario such as shown in FIG. 3. For example, in some cases, one or more imaging devices used to capture images of the interior of the cavity of the patient may be stereo cameras, which could have a larger cross sectional area than may be present in a non-stereo imaging device.

In some versions, a method may be performed to provide visualizations in a multi-camera scenario such as shown in FIG. 3. By way of example only, such a method may be performed in accordance with at least some of the teachings of U.S. patent application Ser. No. 17/528,369, entitled "Surgical Visualization Image Enhancement," filed Nov. 17, 2021, published as U.S. Pat. Pub. No. 2023/0156174 on May 18, 2023, the disclosure of which is incorporated by reference herein in its entirety.

III. EXEMPLARY SURGICAL VISUALIZATION SYSTEMS WITH IMAGING DEVICES FOR 3D SURGICAL IMAGING

In some instances, it may be desirable to provide a surgical visualization system including at least one imaging device (e.g., a stereo camera) that is configured to capture images of an interior of a cavity of a patient, such as the patient's abdominal cavity, without being inserted through the working channel of a corresponding trocar. Such an imaging device may permit a reduction in the quantity of trocars used to access and/or visualize the patient's abdominal cavity during a surgical procedure, and may thereby reduce the size and/or quantity of openings that must be formed through the patient's abdominal wall to accommodate the trocars. In addition, or alternatively, such an imaging device may be self-stabilizing relative to the patient's abdominal cavity so that the surgeon (or other operator) or robotic arm may not be burdened by needing to hold the imaging devices. Each of the examples of surgical visualization systems (200, 300) and imaging devices (210, 310) described below may function in such a manner. While the examples provided below are discussed in the context of visualizing a patient's abdominal cavity, surgical visualization systems (200, 300) and imaging devices (210, 310) may be used to visualize any other region of the patient's anatomy, such as the patient's thoracic cavity, for example.

A. Exemplary Surgical Visualization System with Imaging Thumbtack

FIGS. 5-8 show an example of a surgical visualization system (200) including at least one imaging device in the form of an imaging thumbtack (also referred to as a pushpin) (210) that may be utilized intraoperatively to capture images of an interior of a patient's abdominal cavity (A) in which one or more critical structures (C1, C2) are situated and into which a surgical device (216) is inserted. The surgical device (216) may include an end effector having opposing jaws and/or other structures extending from the distal end of the shaft of the surgical device (216). The surgical device (216) may be any suitable surgical device such as, for example, a dissector, a stapler, a grasper, a clip applier, a monopolar RF electrosurgical instrument, a bipolar RF electrosurgical instrument, and/or an ultrasonic instrument. In the example shown, the surgical visualization system (200) also includes another imaging device in the form of a laparoscope (217) inserted into the abdominal cavity (A). The images captured by the at least one imaging thumbtack (210) and the laparoscope (217) may be combined via image processing techniques (e.g., bundle adjustment or other multi view geometry techniques) to create a complete three-dimensional representation (e.g., a point cloud) of the relevant portion of the interior of the abdominal cavity (A), including the one or more critical structures (C1, C2). As shown, the surgical device (216) may be at least partially inserted through a corresponding trocar (218). While not shown, the laparoscope (217) may similarly be at least partially inserted through a corresponding trocar. The surgical visualization system (200) is similar to the surgical visualization system (10) described above except as otherwise described below.

Figure 6:
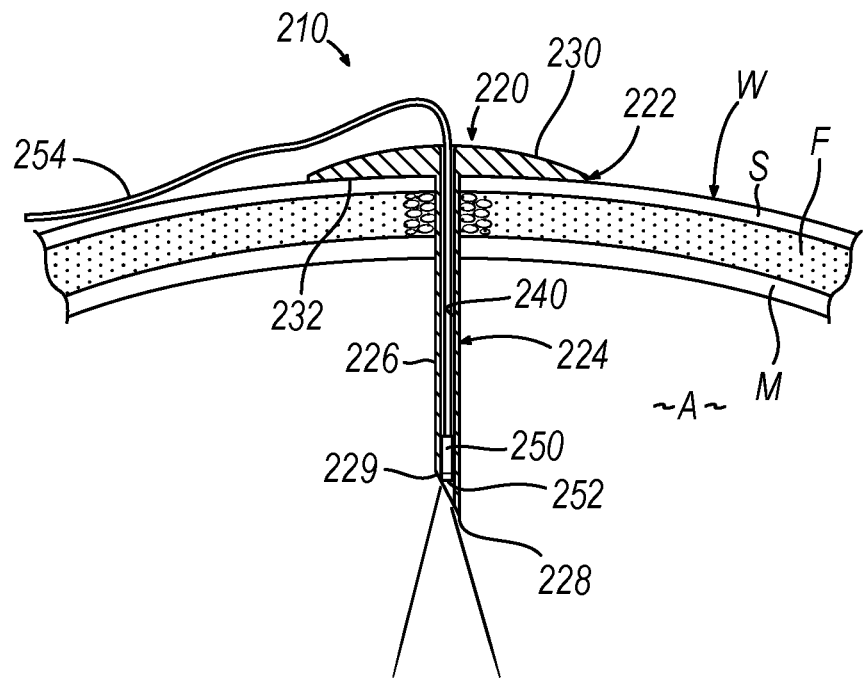
FIG. 6 depicts a cross-sectional side view of the imaging thumbtack of FIG. 5.
Figure 7:
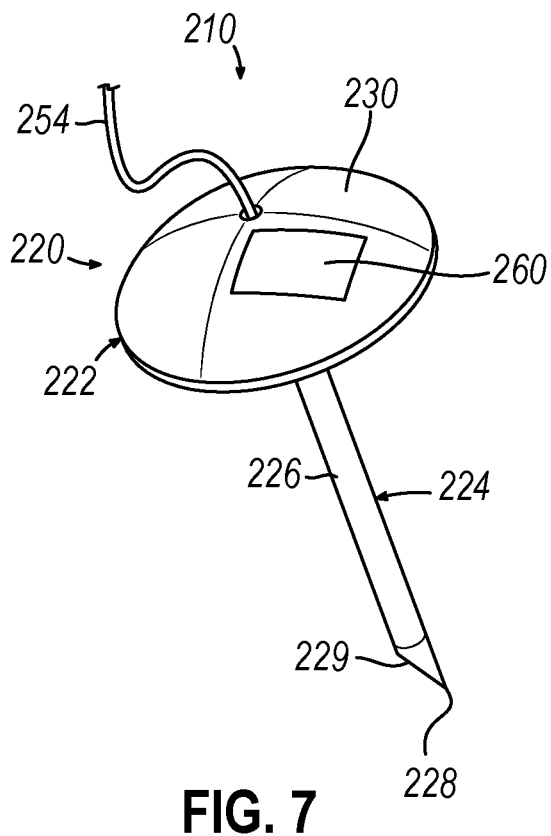
FIG. 7 depicts a top perspective view of the imaging thumbtack of FIG. 5.
Figure 8:
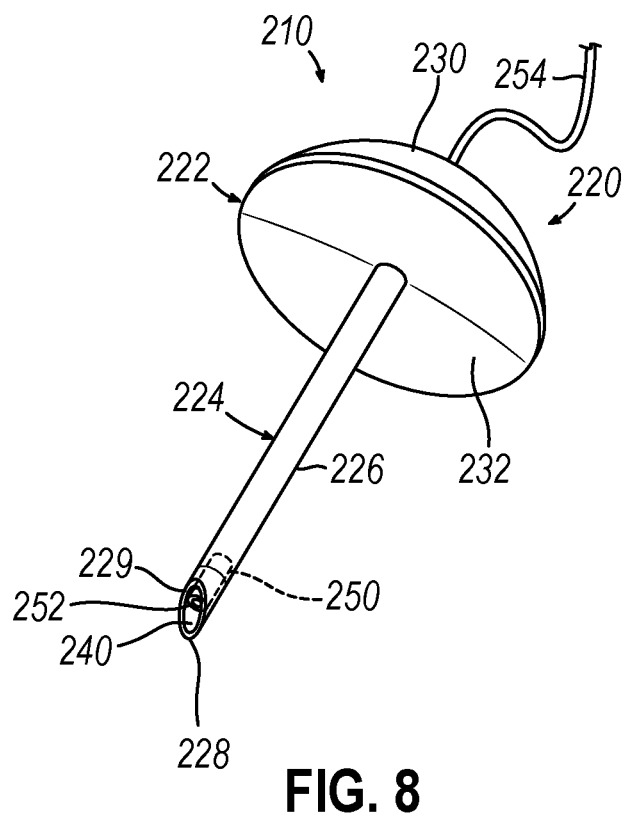
FIG. 8 depicts a bottom perspective view of the imaging thumbtack of FIG. 5.
Figure 9:
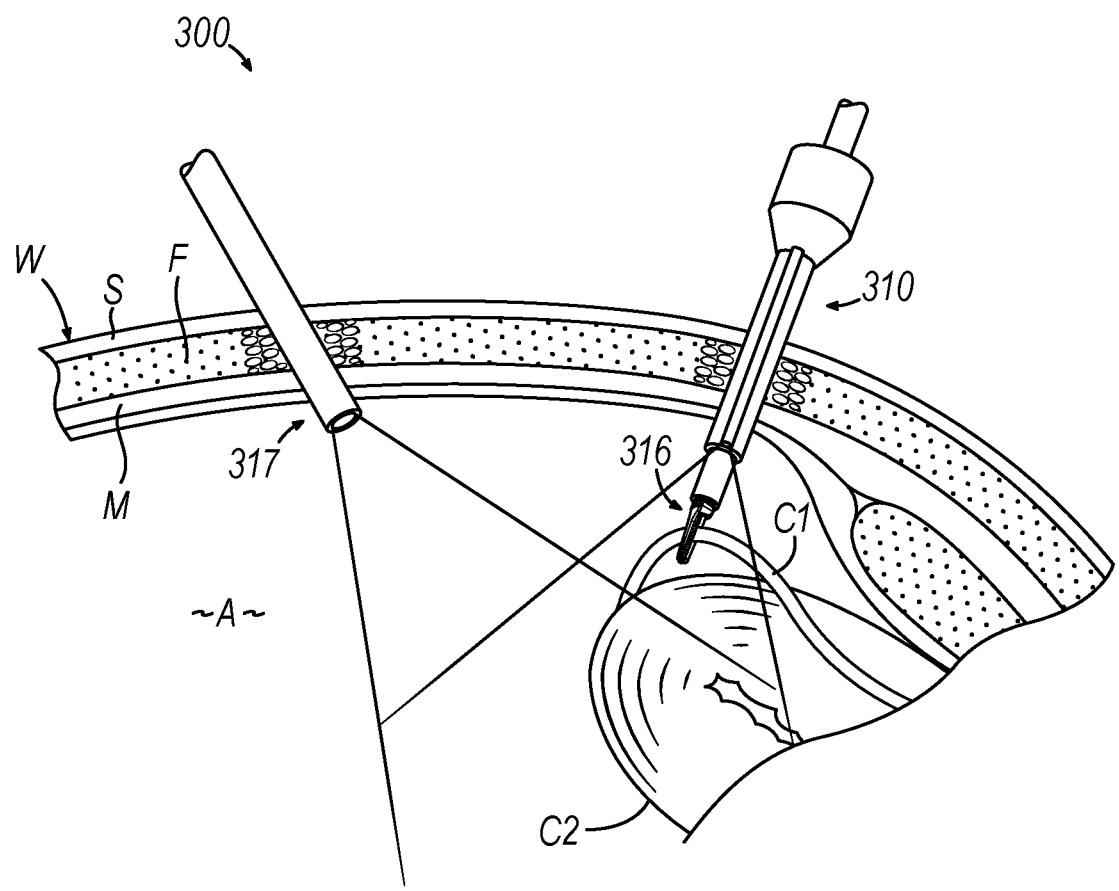
FIG. 9 depicts a schematic view of another exemplary surgical visualization system including a laparoscope and an imaging trocar.

As best shown in FIGS. 6-8, the imaging thumbtack (210) of the present example includes a rigid body (220) including a head (222) and a hypodermic needle (224) extending distally from the head (222) such that the body (220) has a generally T-shaped cross section. In some versions, the body (220) may be formed of a robust biocompatible material, such as surgical stainless steel, so that the imaging thumbtack (210) may be sterilized and reused for multiple surgical procedures. In some other versions, the imaging thumbtack (210) may be constructed to be disposed of after a single use with a patient.

In the example shown, the needle (224) includes a rigid shaft (226) having a proximal end fixedly secured to the head (222) and a sharp distal tip (228) that is configured to pierce tissue. In this regard, it will be appreciated that the abdominal wall (W) includes outward superficial layers and inward deep layers. The superficial layers generally include an outer layer of skin (S) and an inner layer of fat (F); whereas the deeper layers include alternating layers of muscle (M) and fascia (not shown), which are fibrous and flexible with relatively higher tensile strength than the superficial layers. The sharp distal tip (228) may be configured to pierce through each of these layers of tissue (S, F, M) to access the abdominal cavity (A) such that the needle (224) may be inserted percutaneously. In the example shown, the shaft (226) includes a bevel (229) terminating at the sharp distal tip (228) to assist with penetration of the abdominal wall (W) by the sharp distal tip (228).

The shaft (226) may have a sufficiently small outer cross dimension (e.g., diameter) to form a self-sealing opening through the abdominal wall (W) such that sutures may not be required to seal the incision after the needle (224) is withdrawn from the abdominal wall (W). For example, the opening formed through the abdominal wall (W) by the shaft (226) may have a cross-dimension (e.g., diameter) less than or equal to about 3 mm. In this regard, the shaft (226) may have an outer diameter less than or equal to about 2 mm. In some versions, the shaft (226) may have an outer diameter substantially equal to that of needle shafts used for performing fine-needle aspiration biopsies. For example, the needle (224) may be between about 23 gauge and about 25 gauge, such that the shaft (226) may have an outer diameter of between about 0.52 mm and about 0.64 mm. In addition, or alternatively, an outer surface of the shaft (226) of the needle (224) may include a plurality of tissue gripping features such as annular ribs (not shown), which may be configured to grip the layers of tissue (S, F, M) of the abdominal wall (W) through which the needle (224) is inserted, and thereby assist in stabilizing the imaging thumbtack (210) in axial and radial directions while the needle (224) is positioned within the opening formed in the abdominal wall (W).

In the example shown, the head (222) of the imaging thumbtack (210) includes a generally dome-shaped upper surface (230) configured to be pushed downwardly by the operator for inserting the needle (224) through the abdominal wall (W), and a generally flat or slightly contoured lower surface (232) that extends radially outwardly relative to the proximal end of the needle (224) such that the lower surface (232) of the head (222) may abut or otherwise engage a portion of the abdominal wall (W) (e.g., the outer layer of skin (S)) when the needle (224) is fully inserted therethrough. In this manner, the lower surface (232) of the head (222) may provide a positive stop to prevent over-insertion of the needle (224) through the abdominal wall (W). While the upper surface (230) of the present example is generally dome-shaped, it will be appreciated that the upper surface (230) may have any other suitable type of shape, such as flat and/or tapered.

In addition, or alternatively, the lower surface (232) of the head (222) may engage a sufficient portion of the abdominal wall (W) (e.g., the outer layer of skin (S)) to provide the imaging thumbtack (210) with a substantial degree of stability relative to the abdominal wall (W) in the axial and/or radial directions. For example, such engagement may provide the imaging thumbtack (210) with sufficient stability to allow the imaging thumbtack (210) to be substantially fixed against movement relative to the abdominal wall (W). In the example shown, the head (222) has a substantially low profile and is generally flush with the outer layer of skin (S) when the needle (224) is fully inserted through the abdominal wall (W) to minimize the potential risk of a moment arm being applied to the head (222) while the needle (224) is fully inserted through the abdominal wall (W) that might otherwise cause slight pivoting of the imaging thumbtack (210). In this regard, the needle (224) may have a length substantially equal to or slightly greater than a thickness of the abdominal wall (W) so that the sharp distal tip (228) may access the abdominal cavity (A) when the lower surface (232) of the head (222) engages the outer layer of skin (S), for example. In some versions, the needle (224) may have a length of between about 75 mm and about 100 mm.

In this manner, the imaging thumbtack (210) may be self-stabilizing so that the surgeon (or other operator) or robotic arm may not need to hold the imaging thumbtack (210) once the imaging thumbtack (210) has been affixed to the abdominal wall (W) to prevent inadvertent movement of the imaging thumbtack (210) relative to the abdominal wall (W). As shown, the imaging thumbtack (210) may be affixed to the abdominal wall (W) at a location spaced apart from each of the laparoscope (217), the surgical device (216), and the trocar (218), to avoid colliding with or otherwise interfering with any of the laparoscope (217), the surgical device (216), or the trocar (218).

In some versions, the lower surface (232) of the head (222) may be textured or otherwise configured to enhance the frictional engagement between the lower surface (232) of the head (222) and the outer layer of skin (S) to further stabilize the imaging thumbtack (210) relative to the abdominal wall (W). In addition, or alternatively, the lower surface (232) of the head (222) may be at least slightly contoured to complement a curvature of the outer layer of skin (S).

In the example shown, the body (220) of the imaging thumbtack (210) further includes a central bore (240) extending through both the head (222) and the needle (224). The central bore (240) of the present example extends longitudinally along a central axis of the imaging thumbtack (210) between the sharp distal tip (228) and the upper surface (230) of the head (222).

In this regard, the imaging thumbtack (210) of the present example further includes a camera (250) fixedly secured to the body (220) of the imaging thumbtack (210) within the central bore (240) near the sharp distal tip (228). In some versions, the central bore (240) may be sized and shaped to provide an interference fit or a snap-fit between the central bore (240) and the camera (250). It will be appreciated that the camera (250) may be fixedly retained within the central bore (240) in any other suitable manner. The camera (250) of the present example is received within the central bore (240) at or slightly proximally of the bevel (229), such that the camera (250) is substantially surrounded by the shaft (226) in the radial direction. In this manner, the camera (250) may be securely housed within the shaft (226) to avoid interfering with the piercing of the abdominal wall (W) by the sharp distal tip (228).

The camera (250) of the present example includes at least one image sensor (252) configured to capture images of objects within a field of view of the at least one image sensor (252), such as the one or more critical structures (C1, C2) within the interior of the abdominal cavity (A). The at least one image sensor (252) may be in operative communication with a processor (not shown) via one or more wires (254) extending proximally from the camera (250) through the central bore (240). In some versions, the at least one image sensor (252) may be in operative communication with such a processor via a suitable wireless communication protocol. The head (222) of the imaging thumbtack (210) may be configured to provide sufficient space for routing wire(s)

(254) and/or a wireless transmitter and a power source in cases where a wireless communication protocol is used, while having the substantially low profile described above. While the at least one image sensor (252) of the present example is disposed near the sharp distal tip (228) and/or bevel (229), the at least one image sensor (252) may alternatively be disposed substantially proximally of the sharp distal tip (228) and/or bevel (229). In such cases, one or more lenses (not shown) may be disposed near the sharp distal tip (228) and/or bevel (229) for expanding the effective field of view of the at least one image sensor (252).

In some versions, the at least one image sensor (252) may have a cross sectional area less than one square millimeter. For example, the at least one image sensor (252) may include the OV6948 offered by OmniVision Technologies, Inc., which measures 0.575 mm×0.575 mm. In this regard, the camera (250) may include the OV6948 CAMERACUBECHIP offered by OmniVision Technologies, Inc., which measures 0.65 mm×0.65 mm. In some other versions, the camera (250) may be stereoscopic. For example, the camera (250) may include a pair of image sensors (252) spaced apart from each other in a side-by-side arrangement within the central bore (240) to provide stereoscopic visualization of objects within the collective field of view of such a pair of image sensors (252).

In the example shown, the imaging thumbtack (210) further includes a fiducial marker (260) secured (e.g., adhered) to the upper surface (230) of the head (222) to serve as a reference point for identifying the location and/or orientation of the imaging thumbtack (210) relative to the abdominal wall (W), which may be used to determine the location and/or orientation of the at least one image sensor (252) relative to other components of the surgical visualization system (200), such as the laparoscope (217), and/or relative to the surgical device (216). For example, the location of the at least one image sensor (252) may be registered to the laparoscope (217) for bundle adjustment via an exterior camera (not shown) tracking the fiducial marker (260) in three-dimensional space. It will be appreciated that the fiducial marker (260) may be within the non-visual range such that the fiducial maker (260) may be invisible to the surgeon (or other operator). In some versions, the imaging thumbtack (210) may include a position sensor (not shown) in addition to or in lieu of the fiducial marker (260). In some other versions, the location of the at least one image sensor (252) may be registered to the laparoscope (217) for bundle adjustment via analysis of the images captured by the laparoscope (217) and/or by the imaging thumbtack (210), such that the fiducial marker (260) may be omitted.

In some other versions, the imaging thumbtack (210) may include a light emitter (not shown) in addition to or in lieu of the at least one image sensor (252). Such a light emitter may be configured to emit any one or more of structured light, patterned light, regular white light, light having different wavelengths, laser light, etc. For example, structured and/or patterned light emitted by such a light emitter may be used to determine the location and/or orientation of the at least one image sensor (252) in a manner similar to that described above. In addition, or alternatively, the light emitted by such a light emitter may be used to estimate depth of anatomical structures either independently of or in conjunction with the at least one image sensor (252); to reconstruct the three-dimensional surgical scene (e.g., using shape from shading and/or structured light recovery techniques); to enhance the quality of the images captured by the imaging thumbtack (210) and/or by the laparoscope (217); and/or to pose estimate light sources for increased reconstruction accuracy.

In some cases, the light emitted by such a light emitter of the imaging thumbtack (210) may be sufficient to allow the laparoscope (217) to function properly without requiring its own dedicated light emitter so that such a dedicated light emitter may be omitted from the laparoscope (217), thereby enabling the laparoscope (217) to have a reduced size relative to laparoscopes having their own dedicated light emitters.

As noted above, the images captured by the imaging thumbtack (210) and the laparoscope (217) of the surgical visualization system (200) may be combined via image processing techniques to create a complete three-dimensional representation of the relevant portion of the interior of the abdominal cavity (A). In addition, or alternatively, the images captured by the imaging thumbtack (210) and/or the light emitted by imaging thumbtack (210) may be used to enhance the quality of the images captured by the laparoscope (217). For example, the imaging thumbtack (210) may capture images in a region which the laparoscope (217) perceives as being dark, so that such images captured by the imaging thumbtack (210) may be used to augment the images captured by the laparoscope (217).

While a single imaging thumbtack (210) is shown, it will be appreciated that the surgical visualization system (200) may include any suitable number of imaging thumbtacks (210). For example, the surgical visualization system (200) may include a second imaging thumbtack (210) in addition to or in lieu of the laparoscope (217). In addition, or alternatively, the surgical visualization system (200) may include another imaging device incorporated into the trocar (218), such as in a manner similar to that described below. In some cases, the surgical visualization system (200) may include at least four imaging devices to provide a scenario similar to that shown in FIG. 3. In any event, a method may be performed to provide visualizations using images captured by the various imaging devices of surgical visualization system (200) in accordance with at least some of the teachings of U.S. patent application Ser. No. 17/528,369, entitled "Surgical Visualization Image Enhancement," filed Nov. 17, 2021, published as U.S. Pat. Pub. No. 2023/0156174 on May 18, 2023, the disclosure of which is incorporated by reference herein in its entirety.

B. Exemplary Surgical Visualization System with Imaging Trocar

FIGS. 9-12 show an example of another surgical visualization system (300) including at least one imaging device in the form of an imaging trocar (310) that may be utilized intraoperatively to capture images of an interior of a patient's abdominal cavity (A) in which one or more critical structures (C1, C2) are situated and into which a surgical device (316) is inserted (e.g., via the imaging trocar (310)). The surgical device (316) may include an end effector having opposing jaws and/or other structures extending from the distal end of the shaft of the surgical device (316). The surgical device (316) may be any suitable surgical device such as, for example, a dissector, a stapler, a grasper, a clip applier, a monopolar RF electrosurgical instrument, a bipolar RF electrosurgical instrument, and/or an ultrasonic instrument. In the example shown, the surgical visualization system (300) also includes another imaging device in the form of a laparoscope (317) inserted into the abdominal cavity (A) (e.g., via a trocar). The images captured by the at least one imaging trocar (310) (e.g., using a stereo camera having a known calibration) and the laparoscope (317) may be combined via image processing techniques (e.g., bundle adjustment or other multi view geometry techniques) to create a complete three-dimensional representation (e.g., a point cloud) of the relevant portion of the interior of the abdominal cavity (A), including the one or more critical structures (C1, C2). The surgical visualization system (300) is similar to the surgical visualization system (200) described above except as otherwise described below.

Figure 10:
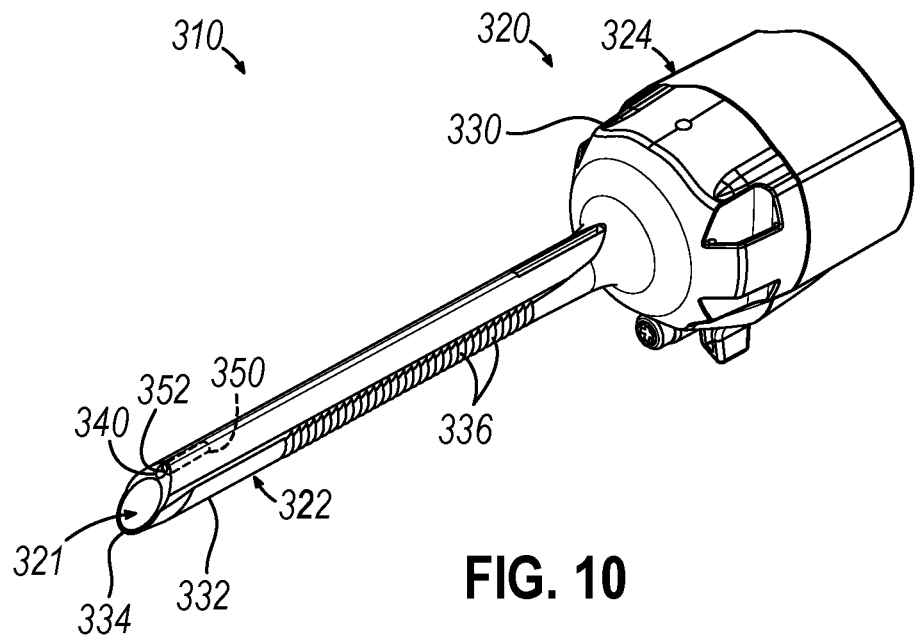
FIG. 10 depicts a perspective view of the imaging trocar of FIG. 9.
Figure 11:
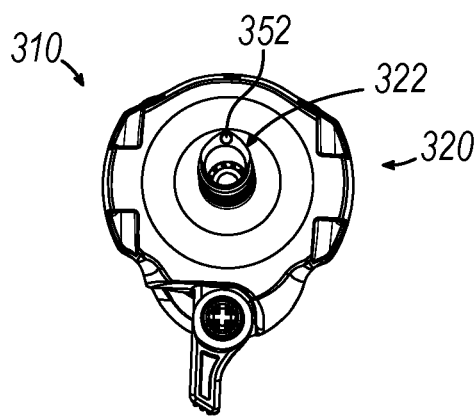
FIG. 11 depicts a bottom plan view of the imaging trocar of FIG. 9.
Figure 12:
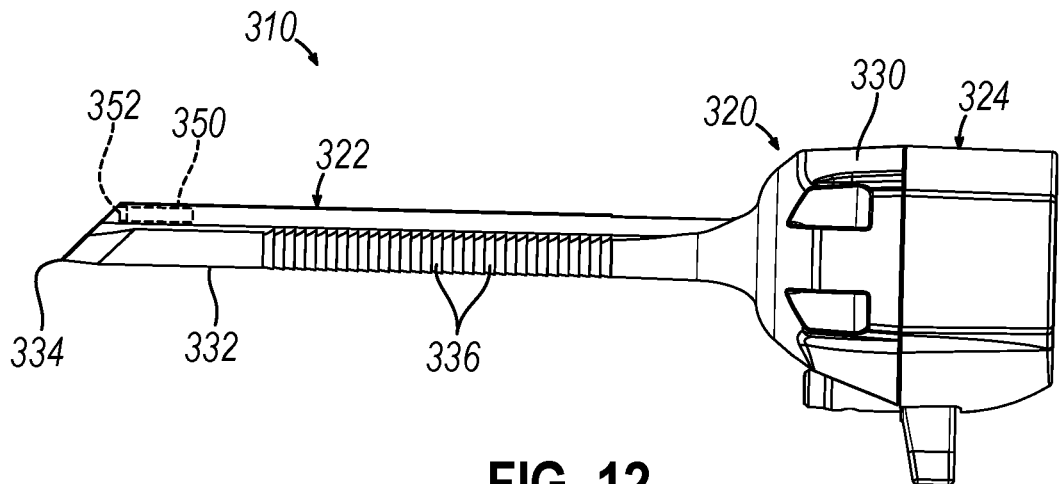
FIG. 12 depicts a side elevation view of the imaging trocar of FIG. 9.

As best shown in FIGS. 10-12, the imaging trocar (310) of the present example includes a cannula assembly (320) having a working channel (321), and an obturator (not shown) configured to be removably inserted coaxially into the working channel (321) for facilitating insertion of the imaging trocar (310) through the abdominal wall (W). Cannula assembly (320) includes a cannula (322) and a seal housing (324) which cooperate to define the working channel (321), which extends longitudinally along a central axis of the imaging trocar (310). In particular, the working channel (321) is defined by a lumen of the cannula (322) in communication with a hollow interior of the seal housing (324). The cannula assembly (320) is configured to receive the surgical device (316) distally through the working channel (321) to provide access to the surgical site within the abdominal cavity (A) of the patient. The seal housing (324) houses a pair of seal structures defining a seal assembly configured to maintain insufflation of the abdominal cavity (A) while permitting passage of the surgical device (316) and tissue fragments along the working channel (321). By way of example only, the seal housing (324) may be configured in accordance with one or more teachings of U.S. Pat. Pub. No. 2019/0090905, entitled "Trocar Seal Assemblies," published Mar. 28, 2019, issued as U.S. Pat. No. 10,792,069 on Oct. 6, 2020, the disclosure of which is incorporated by reference herein; and/or U.S. Pat. Pub. No. 2019/0380742, entitled "Asymmetric Shaft Seal," published Dec. 19, 2019, issued as U.S. Pat. No. 10,820,924 on Nov. 3, 2020, the disclosure of which is incorporated by reference herein.

The cannula (322) of the present version includes a bell-shaped hub (330) at a proximal end thereof, and an elongate generally cylindrical tube (332) extending distally from the hub (330) and terminating at a sharp, angled cannula tip (334) that is configured to pierce through each of the layers of tissue (S, F, M) of the abdominal wall (W). An outer surface of the cannula tube (332) includes a plurality of tissue gripping features in the form of at least partially annular ribs (336) arranged axially along a medial portion of the cannula tube (332) and configured to grip the layers of tissue (S, F, M) of the abdominal wall (W) through which the cannula (322) is inserted, and thereby assist in stabilizing the cannula (322) in axial and radial directions while the cannula (322) is positioned within the opening formed in the abdominal wall (W). In some versions, the cannula (322) may be formed of a robust biocompatible material, such as surgical stainless steel, so that the imaging trocar (310) may be sterilized and reused for multiple surgical procedures. In some other versions, the imaging trocar (310) may be constructed to be disposed of after a single use with a patient. In any event, the tube (332) may have an outer diameter less than or equal to about 5 mm.

In some versions, a shaft of the surgical device (316) may have a cross sectional dimension slightly less than that of the working channel (321) such that the shaft may be slidably received therein. Thus, the imaging trocar (310) and the surgical device (316) may be generally stabilized relative to each other at least in the radial direction when the surgical device (316) is received within the working channel (321). In this manner, the imaging trocar (310) may be stabilized together with the surgical device (316) relative to the abdominal wall (W) at least in the radial direction so that the surgeon (or other operator) or robotic arm may not need to independently hold the imaging trocar (310) during manipulation of the surgical device (316).

In the example shown, the cannula assembly (320) of the imaging trocar (310) further includes an offset bore (340) extending at least partially through the tube (332) of the cannula (322). The offset bore (340) of the present example extends longitudinally parallel to the central axis of the imaging trocar (310) between the angled cannula tip (334) and a proximal region of the tube (332) of the cannula (322).

In this regard, the imaging trocar (310) of the present example further includes a camera (350) fixedly secured to the cannula (322) of the imaging trocar (310) within the offset bore (340) near the angled cannula tip (334). In some versions, the offset bore (340) may be sized and shaped to provide an interference fit or a snap-fit between the offset bore (340) and the camera (350). It will be appreciated that the camera (350) may be fixedly retained within the offset bore (340) in any other suitable manner. While the camera (350) of the present example is fixedly secured to the cannula (322) of the imaging trocar (310) within the offset bore (340), it will be appreciated that the camera (350) may be built into or mounted to the cannula (322) in any suitable manner. For example, the camera (350) may be magnetically coupled with the cannula (322). In other versions, the camera (350) may be fixedly secured to a sheath (not shown) which may be inserted through the working channel (321) and which may permit advancement of the surgical device (316) through the sheath.

The camera (350) of the present example includes at least one image sensor (352) configured to capture images of objects within a field of view of the at least one image sensor (352), such as the one or more critical structures (C1, C2) within the interior of the abdominal cavity (A). The at least one image sensor (352) may be in operative communication with a processor (not shown) via one or more wires (not shown) extending proximally from the camera (350) through the offset bore (340). In some versions, the at least one image sensor (352) may be in operative communication with such a processor via a suitable wireless communication protocol.

In some versions, the at least one image sensor (352) may have a cross sectional area less than one square millimeter. For example, the at least one image sensor (352) may include the OV6948 offered by OmniVision Technologies, Inc., which measures 0.575 mm×0.575 mm. In this regard, the camera (350) may include the OV6948 CAMERACUBECHIP offered by OmniVision Technologies, Inc., which measures 0.65 mm×0.65 mm. In some other versions, the camera (350) may be stereoscopic. For example, the camera (350) may include a pair of image sensors (352) spaced apart from each other in a side-by-side arrangement within the offset bore (340) to provide stereoscopic visualization of objects within the collective field of view of such a pair of image sensors (352).

In some versions, the imaging trocar (310) may include a fiducial marker and/or a position sensor (not shown) secured to the cannula (322), which may be used to determine the location and/or orientation of the at least one image sensor (352) relative to other components of the surgical visualization system (300), such as the laparoscope (317), and/or relative to the surgical device (316) in a manner similar to that described above. In addition, or alternatively, the imaging trocar (310) may include an inertial measurement unit (IMU) secured to the cannula (322) for measuring an orientation of the imaging trocar (310) relative to the abdominal wall (W), for example, and/or for assisting in the registration of the at least one image sensor (352) to the laparoscope (317).

In some other versions, the imaging trocar (310) may include a light emitter (not shown) in addition to or lieu of the at least one image sensor (352). Such a light emitter may be configured to emit any one or more of structured light, patterned light, regular white light, light having different wavelengths, laser light, etc. For example, structured and/or patterned light emitted by such a light emitter may be used to determine the location and/or orientation of the at least one image sensor (352) in a manner similar to that described above. In addition, or alternatively, the light emitted by such a light emitter may be used to estimate depth of anatomical structures either independently of or in conjunction with the at least one image sensor (352); to reconstruct the three-dimensional surgical scene (e.g., using shape from shading and/or structured light recovery techniques); to enhance the quality of the images captured by the imaging trocar (310) and/or by the laparoscope (317); and/or to pose estimate light sources for increased reconstruction accuracy. In some cases, the light emitted by such a light emitter of the imaging trocar (310) may be sufficient to allow the laparoscope (317) to function properly without requiring its own dedicated light emitter so that such a dedicated light emitter may be omitted from the laparoscope (317), thereby enabling the laparoscope (317) to have a reduced size relative to laparoscopes having their own dedicated light emitters.

As noted above, the images captured by the imaging trocar (310) and the laparoscope (317) of the surgical visualization system (300) may be combined via image processing techniques to create a complete three-dimensional representation of the relevant portion of the interior of the abdominal cavity (A). In addition, or alternatively, the images captured by the imaging thumbtack (210) and/or the light emitted by imaging thumbtack (210) may be used to enhance the quality of the images captured by the laparoscope (317). For example, the imaging thumbtack (210) may capture images in a region which the laparoscope (317) perceives as being dark, so that such images captured by the imaging thumbtack (210) may be used to augment the images captured by the laparoscope (317).

While a single imaging trocar (310) is shown, it will be appreciated that the surgical visualization system (300) may include any suitable number of imaging trocars (310). For example, the surgical visualization system (300) may include a second imaging trocar (310) in addition to or in lieu of the laparoscope (317), which may facilitate insertion of a second surgical device (not shown) through such a second imaging trocar (310). In addition, or alternatively, the surgical visualization system (200) may include another imaging device incorporated into the surgical device (316), such as in a manner similar to that described above with respect to the imaging trocar (310). In some versions, the surgical visualization system (300) may include at least one imaging thumbtack (210). In addition, or alternatively, the surgical visualization system (200) may include at least four imaging devices to provide a scenario similar to that shown in FIG. 3. In any event, a method may be performed to provide visualizations using images captured by the various imaging devices of surgical visualization system (300) in accordance with at least some of the teachings of U.S. patent application Ser. No. 17/528,369, entitled "Surgical Visualization Image Enhancement," filed Nov. 17, 2021, published as U.S. Pat. Pub. No. 2023/0156174 on May 18, 2023, the disclosure of which is incorporated by reference herein in its entirety.

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical imaging device comprising: (a) a rigid body comprising: (i) an elongate member extending longitudinally along a central axis to a sharp distal tip, wherein the sharp distal tip is configured to pierce through tissue to access an interior of a cavity of a patient, and (ii) a bore extending longitudinally through at least a portion of the elongate member; and (b) a camera secured to the elongate member of the rigid body within the bore of the rigid body, wherein the camera is adapted to capture images of the interior of the cavity of the patient when the sharp distal tip has pierced through the tissue to access the interior of the cavity of the patient.

Example 2

The surgical imaging device of Example 1, wherein the camera comprises a stereoscopic camera.

Example 3

The surgical imaging device of any one or more of Examples 1 through 2, wherein the rigid body further comprises a head, wherein the elongate member extends distally from the head.

Example 4

The surgical imaging device of Example 3, wherein the head comprises a tissue engagement surface extending radially outwardly relative to the elongate member, wherein the tissue engagement surface is adapted to engage an exterior surface of the tissue when the sharp distal tip has pierced through the tissue to access the interior of the cavity of the patient.

Example 5

The surgical imaging device of any one or more of Examples 3 through 4, further comprising a fiducial marker secured to the head.

Example 6

The surgical imaging device of any one or more of Examples 1 through 5, wherein the bore extends longitudinally along the central axis of the elongate member.

Example 7

The surgical imaging device of any one or more of Examples 1 through 6, wherein the bore extends longitudinally parallel to the central axis of the elongate member.

Example 8

The surgical imaging device of any one or more of Examples 1 through 7, wherein the elongate member is sized to form a self-sealing opening through the tissue.

Example 9

The surgical imaging device of any one or more of Examples 1 through 8, wherein the elongate member comprises a hypodermic needle.

Example 10

The surgical imaging device of any one or more of Examples 1 through 9, wherein the elongate member comprises a trocar cannula.

Example 11

A surgical visualization system comprising: (a) a plurality of surgical imaging devices of any one or more of Examples 1 through 10; and (b) a processor in operative communication with each camera of the plurality of surgical imaging devices.

Example 12

The surgical visualization system of Example 11, wherein the processor is configured to receive a set of points corresponding to each image captured by each camera of the plurality of surgical imaging devices.

Example 13

The surgical visualization system of Example 12, wherein the processor is configured to generate a three-dimensional point cloud representing the interior of the cavity of the patient based on combining the sets of points received from each camera of the plurality of surgical imaging devices.

Example 14

The surgical visualization system of Example 13, wherein the processor is configured to combine the sets of points received from the plurality of cameras using bundle adjustment.

Example 15

The surgical visualization system of any one or more of Examples 11 through 14, wherein the plurality of surgical imaging devices comprises at least four surgical imaging devices.

Example 16

A surgical imaging device comprising: (a) a rigid body comprising: (i) a head, (ii) a needle extending distally from the head along a central axis to a sharp distal tip, wherein the sharp distal tip is configured to pierce through tissue to access an interior of a cavity of a patient, and (iii) a bore extending through at least a portion of the needle along the central axis; and (b) a camera secured to the needle of the rigid body within the bore of the rigid body, wherein the camera is adapted to capture images of the interior of the cavity of the patient when the sharp distal tip has pierced through the tissue to access the interior of the cavity of the patient.

Example 17

The surgical imaging device of Example 16, wherein the head comprises a tissue engagement surface extending radially outwardly relative to the needle, wherein the tissue engagement surface is adapted to engage an exterior surface of the tissue when the sharp distal tip has pierced through the tissue to access the interior of the cavity of the patient.

Example 18

The surgical imaging device of any one or more of Examples 16 through 17, wherein the needle comprises a hypodermic needle.

Example 19

A surgical imaging device comprising: (a) a rigid body comprising: (i) a trocar cannula extending longitudinally along a central axis to a sharp distal tip, wherein the sharp distal tip is configured to pierce through tissue to access an interior of a cavity of a patient, (ii) a working lumen extending through the trocar cannula along the central axis, wherein the working lumen is configured to guide a surgical device shaft distally through the trocar cannula for accessing the interior of the cavity of the patient, and (iii) a bore extending through at least a portion of the trocar cannula parallel to the central axis; and (b) a camera secured to the trocar cannula of the rigid body within the bore of the rigid body, wherein the camera is adapted to capture images of the interior of the cavity of the patient when the sharp distal tip has pierced through the tissue to access the interior of the cavity of the patient.

Example 20

The surgical imaging device of Example 19, wherein the camera is secured to the trocar cannula via at least one of a magnetic coupling or a sheath.

V. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may be designed to be disposed of after a single use, or they may be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that may penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical imaging device comprising:
   (a) a rigid body comprising:
      (i) an elongate member extending longitudinally along a central axis to a sharp distal tip, wherein the sharp distal tip is configured to pierce through tissue to access an interior of a cavity of a patient, and
      (ii) a bore extending longitudinally through at least a portion of the elongate member; and
   (b) a camera secured to the elongate member of the rigid body within the bore of the rigid body between a proximal portion of the bore and a distal portion of the bore, wherein the proximal portion of the bore is fluidly isolated from the distal portion of the bore, wherein the camera is adapted to capture images of the interior of the cavity of the patient when the sharp distal tip has pierced through the tissue to access the interior of the cavity of the patient,
   wherein the elongate member comprises a hypodermic needle.

2. The surgical imaging device of claim 1, wherein the camera comprises a stereoscopic camera.

3. The surgical imaging device of claim 1, wherein the rigid body further comprises a head, wherein the elongate member extends distally from the head.

4. The surgical imaging device of claim 3, further comprising a fiducial marker secured to the head.

5. The surgical imaging device of claim 1, wherein the bore extends longitudinally along the central axis of the elongate member.

6. The surgical imaging device of claim 1, wherein the elongate member is sized to form a self-sealing opening through the tissue.

7. A surgical visualization system comprising:
   (a) a plurality of surgical imaging devices of claim 1; and
   (b) a processor in operative communication with each camera of the plurality of surgical imaging devices.

8. The surgical visualization system of claim 7, wherein the processor is configured to receive a set of points corresponding to each image captured by each camera of the plurality of surgical imaging devices.

9. The surgical visualization system of claim 8, wherein the processor is configured to generate a three-dimensional point cloud representing the interior of the cavity of the patient based on combining the sets of points received from each camera of the plurality of surgical imaging devices.

10. The surgical visualization system of claim 9, wherein the processor is configured to combine the sets of points received from the plurality of cameras using bundle adjustment.

11. The surgical visualization system of claim 7, wherein the plurality of surgical imaging devices comprises at least four surgical imaging devices.

12. The surgical imaging device of claim 1, wherein the elongate member has a length of about 75 mm.

13. The surgical imaging device of claim 1, wherein an outer surface of the elongate member includes a plurality of tissue gripping features configured to grip the tissue pierced by the sharp distal tip.

14. The surgical imaging device of claim 1, wherein the camera is positioned along the central axis and is fixedly secured to the elongate member of the rigid body.

15. A surgical imaging device comprising:
   (a) a rigid body comprising:
      (i) an elongate member extending longitudinally along a central axis to a sharp distal tip, wherein the sharp distal tip is configured to pierce through tissue to access an interior of a cavity of a patient, and
      (ii) a bore extending longitudinally through at least a portion of the elongate member; and
   (b) a camera secured to the elongate member of the rigid body within the bore of the rigid body between a proximal portion of the bore and a distal portion of the bore, wherein the proximal portion of the bore is fluidly isolated from the distal portion of the bore, wherein the camera is adapted to capture images of the interior of the cavity of the patient when the sharp distal tip has pierced through the tissue to access the interior of the cavity of the patient, wherein the rigid body further comprises a head, wherein the elongate member extends distally from the head, wherein the head comprises a tissue engagement surface extending radially outwardly relative to the elongate member, wherein the tissue engagement surface is adapted to engage an exterior surface of the tissue when the sharp distal tip has pierced through the tissue to access the interior of the cavity of the patient.

16. A surgical imaging device comprising:
(a) a rigid body comprising:
  (i) an elongate member extending longitudinally along a central axis to a sharp distal tip, wherein the sharp distal tip is configured to pierce through tissue to access an interior of a cavity of a patient, and
  (ii) a bore extending longitudinally through at least a portion of the elongate member; and
(b) a camera secured to the elongate member of the rigid body within the bore of the rigid body, wherein the bore is sized and shaped to provide an interference fit between the bore and the camera, wherein the camera is adapted to capture images of the interior of the cavity of the patient when the sharp distal tip has pierced through the tissue to access the interior of the cavity of the patient, wherein the elongate member comprises a hypodermic needle.

17. The surgical imaging device of claim 16, wherein the rigid body further comprises a head, wherein the elongate member extends distally from the head.

18. The surgical imaging device of claim 17, wherein the head comprises a tissue engagement surface extending radially outwardly relative to the elongate member, wherein the tissue engagement surface is adapted to engage an exterior surface of the tissue when the sharp distal tip has pierced through the tissue to access the interior of the cavity of the patient.

19. The surgical imaging device of claim 18, wherein the tissue engagement surface is curved to complement a curvature of the exterior surface of the tissue.

20. The surgical imaging device of claim 16, wherein the camera is positioned along the central axis and is fixedly secured to the elongate member of the rigid body.

\* \* \* \* \*